(12) United States Patent
Coulomb et al.

(10) Patent No.: US 9,982,217 B2
(45) Date of Patent: May 29, 2018

(54) ALIPHATIC NITRILE WITH ROSY ODOR

(71) Applicant: Firmenich SA, Geneva (CH)

(72) Inventors: Julien Coulomb, Geneva (CH); Nicolas Guichard, Feigeres (FR)

(73) Assignee: Firmenich SA, Geneva (CH)

( * ) Notice: Subject to any disclaimer, the term of this patent is extended or adjusted under 35 U.S.C. 154(b) by 0 days. days.

(21) Appl. No.: 15/533,497

(22) PCT Filed: Dec. 3, 2015

(86) PCT No.: PCT/EP2015/078440
§ 371 (c)(1),
(2) Date: Jun. 6, 2017

(87) PCT Pub. No.: WO2016/091699
PCT Pub. Date: Jun. 16, 2016

(65) Prior Publication Data
US 2017/0335235 A1    Nov. 23, 2017

(30) Foreign Application Priority Data
Dec. 8, 2014 (EP) .................................... 14196719

(51) Int. Cl.
*C11D 3/50* (2006.01)
*C11B 9/00* (2006.01)
*C07C 255/31* (2006.01)
*C11D 3/00* (2006.01)

(52) U.S. Cl.
CPC .......... *C11B 9/0034* (2013.01); *C07C 255/31* (2013.01); *C11D 3/001* (2013.01); *C11D 3/50* (2013.01); *C07C 2601/14* (2017.05); *C07C 2601/16* (2017.05)

(58) Field of Classification Search
CPC ................................................... C07C 255/31
See application file for complete search history.

(56) References Cited

U.S. PATENT DOCUMENTS

| 4,396,670 | A | 8/1983 | Sinclair | |
|---|---|---|---|---|
| 6,069,125 | A | 5/2000 | Pesaro | |
| 2011/0308556 | A1* | 12/2011 | Smets | A61K 8/738 134/26 |
| 2012/0329696 | A1* | 12/2012 | Denutte | C07C 33/14 510/103 |

FOREIGN PATENT DOCUMENTS

| EP | 1637581 A1 | 3/2006 |
|---|---|---|
| WO | WO1997016512 | 5/1997 |
| WO | WO2001041915 A1 | 6/2001 |
| WO | WO2006133592 A1 | 12/2006 |

OTHER PUBLICATIONS

International Preliminary Report on Patentability, Appl. No. PCT/EP2015/078440, dated Jun. 13, 2017.
International Search Report and Written Opinion, application PCT/EP2015/078440 dated Feb. 17, 2016.
Bône et al., "Microencapsulated Fragrances in Melamine Formaldehyde Resins", Chimia, 2011, vol. 65, No. 3, pp. 177-181.
Dibiase et al., "Direct Synthesis of α,β-Unsaturated Nitriles from Acetonitrile and Carbonyl Compunds", J. of Organic Chemistry, 1979, vol. 44, No. 25, pp. 4640-4649.
Dietrich et al., "Amino resin microcapsules I", Acta Polymerica, 1989, vol. 40, No. 4, pp. 243-251.
Dietrich et al., "Amino resin microcapsules II", Acta Polymerica, 1989, vol. 40, No. 5, pp. 325-331.
Dietrich et al., "Amino resin microcapsules III", Acta Polymerica, 1989, vol. 40, No. 11, pp. 683-690.
Dietrich et al., "Amino resin microcapsules IV", Acta Polymerica, 1990, vol. 41, No. 2, pp. 91-95.
Lee et al., "Microencapsulation of fragrant oil via in situ polymerization", J. Microencapsulation, 2002, vol. 19, No. 5, pp. 559-569.

* cited by examiner

*Primary Examiner* — John R Hardee
(74) *Attorney, Agent, or Firm* — Winston & Strawn LLP

(57) ABSTRACT

The present invention concerns compound of formula

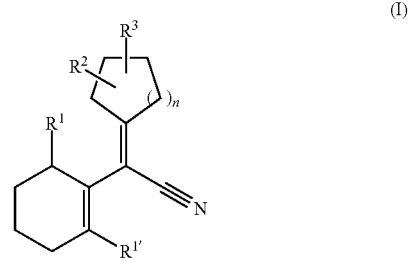

(I)

in the form of any one of its stereoisomers or a mixture thereof, and wherein $R^1$ and $R^{1'}$, independently from each other, represent a hydrogen atom or a methyl group provided that one of said groups represent a hydrogen atom and the other a methyl group; $R^2$ and $R^3$, independently from each other, represent substituents of the saturated ring and are a hydrogen atom or a $C_{1-3}$ alkyl group; and n is an integer varying between 1 and 4; and their use in perfumery to impart odor notes of the floral, rosy type.

10 Claims, No Drawings

ALIPHATIC NITRILE WITH ROSY ODOR

RELATED APPLICATIONS

This application is a national stage application under 35 U.S.C § 371 filing of International Patent Application PCT/EP2015/078440, filed Dec. 3, 2015, which claims the benefit of European patent application n° 14196719.0 filed Dec. 8, 2014.

TECHNICAL FIELD

The present invention relates to the field of perfumery. More particularly it concerns the use as perfuming ingredient of compounds of formula (I) as defined below, which are useful perfuming ingredients of floral, rosy type. Therefore, following what is mentioned herein, the present invention comprises the invention's compound as part of a perfuming composition or of a perfuming consumer product.

PRIOR ART

To the best of our knowledge, the invention's compounds are novel.

To the best of our knowledge, the closest analogue known in the perfumery is the chemical known as Petalia® (2-cyclohexylidene-2-(o-tolyl)acetonitrile; origin: Givaudan, Vernier, Switzerland) described in WO 20061133592 and describes as having fruity, rosy, lychee, palmarosa and rosacetol odor notes.

However, although the invention's compounds possess odor profiles having some similarity with the ones of the prior art compounds, they differ from the latter by having a significantly different chemical structure.

This prior art document does not report or suggest any organoleptic properties of the compounds of formula (I) and does not report or suggest any use of said compounds in the field of perfumery.

DESCRIPTION OF THE INVENTION

We have now surprisingly discovered that a compound of formula

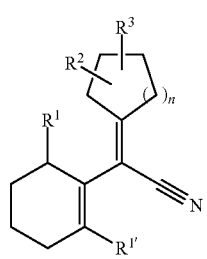

(I)

in the form of any one of its stereoisomers or a mixture thereof, and wherein $R^1$ and $R^{1'}$, independently from each other, represent a hydrogen atom or a methyl group provided that one of said groups represents a hydrogen atom and the other a methyl group;

$R^2$ and $R^3$, independently from each other, represent substituents of the saturated ring and are a hydrogen atom or a alkyl group; and n is an integer varying between 1 and 4;

can be used as perfuming ingredient, for instance to impart odor notes of the floral type, e.g. rosy type.

For the sake of clarity, by the expression "any one of its stereoisomers", or the similar, it is meant the normal meaning understood by a person skilled in the art, i.e. that the invention's compound can be a pure enantiomer (if chiral) or diastereomer.

For the sake of clarity, by the expression "$R^2$ and $R^3$ represent substituents of the saturated ring", or the similar, it is meant the normal meaning understood by a person skilled in the art, i.e. that said groups can be hound to the saturated ring at any one of the available positions.

According to any one of the above embodiments of the invention, said compounds (I) are $C_{14}$-$C_{19}$ compounds.

According to any one of the above embodiments of the invention, a is an integer varying between 1 and 2. More preferably n is equal to 2.

According to any one of the above embodiments of the invention, $R^2$ and $R^3$, independently from each other, represent a hydrogen atom or a methyl group. More preferably $R^2$ represents a hydrogen atom or a methyl group and $R^3$ represents a hydrogen atom.

According to a particular embodiment of the invention, $R^1$ represents a hydrogen atom and $R^{1'}$ represents a methyl group.

According to a particular embodiment of the invention, compound of formula (I) is in the form of a mixture of regioisomers containing at least 80% of both regioisomers wherein, for one regioisomer, $R^1$ represents a hydrogen atom and $R^{1'}$ represents a methyl group and for the second regioisomer; $R^1$ represents a methyl group and $R^{1'}$ represents a hydrogen atom (e.g. 2-cyclohexylidene-2-(2-methylcyclohex-1-en-1-yl)acetonitrile and 2-cyclohexylidene-2-(6-methylcyclohex-1-en-1-yl)acetonitrile). Preferably compound of formula (I) is in the form of a mixture of regioisomers containing at least 50% of regioisomer wherein $R^1$ represents a hydrogen atom and $R^{1'}$ represents a methyl group (e.g. 2-cyclohexylidene-2-(2-methcyclohex-1-en-1-yl)acetonitrile). Even more preferably, compound of formula (I) is in the form of a mixture of regioisomers containing at least 80% regioisomer wherein $R^1$ represents a hydrogen atom and $R^{1'}$ represents a methyl group of (e.g. 2-cyclohexylidene-2-(2-methylcyclohex-1-en-1-yl) acetonitrile).

As specific examples of the invention's compound, one may cite, as non-limiting example, a mixture of regioisomer containing 2-cyclohexylidene-2-(2-methylcyclohex-1-en-1-yl) acetonitrile and 2-cyclohexylidene-2-(6-methylcyclohex-1-en-1-yl)acetonitrile in a respective molar ratio of 94:6, which possesses an odor characterized by a nice floral, rosy and balsamic note with a slightly green aspect. The organoleptic aspect of this compound reminds 2,2,2-trichloro-1-phenylethyl acetate with the advantage of not containing halides. This compound possesses a note extremely tenacious on dry laundry and for several days. Its organoleptic character differentiates slightly from the prior art compound (2-cyclohexylidene-2-(o-tolyl)acetonitrile) by having a more red fruit, anisic and rosy note slightly metallic.

As other example, one may cite a mixture of regioisomer containing 2-cyclohexylidene-2-(6-methylcyclohex-1-en-1-yl)acetonitrile and 2-cyclohexylidene-2-(2-methylcyclohex-1-en-1-yl) acetonitrile in a respective, molar ratio of 95:5, which possesses an odor similar to the one mentioned above but distinguishing itself by having a fatty, chemical and nitrite note.

As other example, one may cite a mixture of regioisomer containing 2-(2-methylcyclohex-1-en-1-yl)-2-(3-methylcyclohexydene) acetonitrile and 2-(6-methylcyclohex-1-en-1-yl)-2-(3-methylcyclohexylidene) acetonitrile which possesses a floral, orange flower and phenolic odor note.

The organoleptic profile of the invention's compounds is very similar to prior art compound Petalia®. Such similitude of odor properties is particularly surprising, since the replacement of an aryl group by a cyclohexenyl group is known to dramatically change the physic-chemical properties of a compound (such as polarity or π-donation ability) and therefore its interaction with the olfactive receptors. Surprisingly, despite of the structural modification, i.e. the invention's compounds have the same carbon atom number than Petalia® but lose the aromatic part of the prior art compound, the invention's compounds possess a floral, rosy note typical of Petalia®. The rosy note is surprisingly observed for the invention's compound.

The odor of the invention's compounds is also kicking, or not possess in significant, jasmine, fruity or salicinate notes.

As mentioned above, the invention concerns the use of a compound of formula (I) as perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethanol or ethyl citrate, which are the most commonly used. For the compositions which comprise both a perfumery carrier and a perfumery base, other suitable perfumery carriers than those previously specified can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin BASF).

As solid carrier it is meant a material where the perfuming composition or some element of the perfuming composition can be chemically or physically bound. In general such solid carrier are employed either to stabilize the composition, either to control the rate of evaporation of the compositions or of some ingredients. The employment of solid carrier is of current use in the art and a person skilled in the art knows how to reach the desired effect. However by way of non-limiting example as solid carriers one may cite absorbing gums or polymers or inorganic material, such as porous polymers, cyclodextrines, wood based materials, organic or inorganic gels, clays, gypsum talc or zeolites.

As other example of solid carrier one may cite encapsulating materials. Examples of such materials may comprise wall-forming and plasticizing, materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schrillenreibe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques are have been described in the prior art), and optionally in presence of polymeric stabilizer or a a cationic copolymer.

In particular, as resins one may cite the ones produced by the polycondensation an aldehyde (e.g. formaldehyde, 2,2-dimethoxyethanal, glyoxal, glyoxylic acid or glycolaldehyde and mixtures thereof) with an amine, namely area, benzoguanamine, glycoluryl, melamine, methylol melamine, methylated methylol melamine, guanazole and the like as well as mixtures thereof. Alternatively one may use preformed resins alkylotated polyamines such as those commercially available under the trademark Urac® (origin: Cytec Technology Corp.), Cy mel® (origin: Cytec Technology Corp.), Urecoll® or Luracoll® (origin: BASF).

In particular, as resins one may cite the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following; prior art methods that are also further detailed and exemplified in the patent literature, U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al. in Journal of Microencapsulation, 2002 vol. 19, pages 559-569, international patent publication WO 01/41915 or yet the article of S. Bône et al, in Chimia, 2011, vol. 65, pages 177-181.

By "perfumery base" we mean here a composition comprising at least one perfuming co-ingredient.

Said perfuming co-ingredient is not of formula (I). Moreover, by "perfuming co-ingredient" it is meant here a compound, which n used in a perfuming preparation or a composition to impart a hedonic effect. In other words such a co-ingredient, to be considered as bet as a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them an the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitrites, terpenoids, nitrogenous or sulphurous heterocyclic compounds and essential oils, and said perfuming co-ingredients can be of natural or synthetic origin.

In particular one may cue perfuming co-ingredients knows for having a similar olfactive note, such as:

In particular one may cite perfuming co-ingredients which are commonly used in perfume formulations, such as Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, Citronellol, phenylethanol, 3-(4-tert-butylphenyl)-2-methylpropanal, hexylcinnamic aldehyde, beta acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool cis-7-P-menthanol, Propyl (S)-2-(1,1-dimethyl-propoxy)propanoate, 2-methoxynaphthalene, 2,2,2-trichloro-1-phenyethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecane-dione, pentadecenolide, 3-Methyl-5-cyclopentadecen-1-one, 1,3,4,6,7,8-hexahydro-4,6,6,7,8,8-hexamethyl-cyclopenta-g-2-benzopyrane, (1S,1R'-2-[1-(3',3'-dimethyl-cyclohexyl)ethoxy]-2-methylpropyl propanoate, pentadecanolide and/or (1S,1'R)-[1-(3',3'-Dimethyl-cyclohexyl) ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'RZ,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol, Methyl cedryl ketone, 5-(2,2,3-trimethyl-3-cyclopente-nyl)-3-methylpentan-2-ol, 1-(2,3,8,8-tetramethyl-1,2,3, 4,6,7,8,8a-octahydronaphthalen-2-yl)ethan-1-one and/ or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imputing additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or cheating agents, such as BHT), color agents (e.g. dyes and/or pigments), preservative (e.g. antibacterial or antimicrobial or antifungi or anti irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented b a perfuming consumer product comprising, as perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive of amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a splash or eau de perfume, a cologne or an shave or after-shave lotion; a fabric care product, such as a liquid or solid detergent, a fabric softener, a fabric refresher, an ironing water, a paper, or a bleach, carpet cleaners, curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a skin cream or lotion, a vanishing cream or a deodorant or antiperspirant (e.g. a spray or roll on), hair remover, tanning or sun or after sun product, nail products, skin cleansing a makeup); or a skin-care product (e.g. a perfumed soap, shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.,); or a home care product, such as a mold remover, furnisher care, wipe, a dish detergent or hard-surface (e.g. a floor, bath, sanitary or a windows) detergent a leather care product; a car care product, such as a polish, waxes or a plastic cleaners.

Some of the above-mentioned consumer product may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

The invention's compounds can be prepared according to a method reported in the literature or standard methods known in the art as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

a) Preparation of mixture of 2-(2-methylcyclohexylidene)acetonitrile, 2-(6-methylcyclohex-1-en-1-yl) acetonitrile and 2-(2-methylcyclohex-1-en-1-yl) acetonitrile (58:5:7)

To a solution of KOH 85% (33.5 g, 508 mmol, 1 equiv.) in refluxing acetonitrile (350 mL) was added a solution of 2-methylcyclohexanone (61.7 mL, 508 mmol, 1 equiv.) acetonitrile (150 mL) dropwise over a 20 min-period. The reaction was refluxed for 4 h before being quenched with water. The aqueous layer was extracted three times with diethyl ether, the combined organic extracts were washed with water twice, dried over sodium sulfate and the solvent was evaporated. The residue was purified by distillation under reduced pressure (15 mbar, 130° C.) to provide acetonitrile compound (52.8 g, 77% yield) as a colorless oil and a 58:5:37 mixture of regioisomers. Spectral data were consistent to those described in the literature (DiBiase, S. A.; Lipisko, B. A.; Haag, A.; Wolak, R. A.; Gokel, G. W. *J. Org. Chem* 1979, 44, 4640-4649).

b) Preparation of Mixture of 2-cyclohexylidene-2-(2-methylcyclohex-1-en-1-yl) acetonitrile and 2-cyclohexylidene-2-(6-methylcyclohex-1-en-1-yl)acetonitrile (94:6)

To a solution of nitrite compound obtained in step a) (11.2 g, 83 mmol, 1 equiv.) and cyclohexanone (42.9 mL, 414 mmol, 5 equiv.) in NMP (50 mL) was added KOH (6.56 g, 99 mmol, 1.2 equiv.) and the reaction was stirred at 80° C. for 3 days before being poured onto cracked ice (150 g). The reaction was quenched with a 10% aqueous solution of HCl and the suspension was filtered. The filtrate was extracted three times with diethyl ether, the combined organic extracts were washed with brine, dried over sodium sulfate and the solvent was evaporated. The residue was purified by bulb-to-bulb distillation (0.2 mbar, 130° C.) and flash column chromatography on silica gel (Heptane/AcOEt 99:1) to afford a mixture of regioisomers containing 2-cyclohexylidene-2-(2-methylcyclohex-1-en-1-yl)acetonitrile and 2-cyclohexylidene-2-(6-methylcyclohex-1-en-1-yl)acetonitrile (12.5 g, 70% yield) as a colorless oil and in a 94:6 molar ratio.
Major isomer:
$^1$H NMR (CDCl$_3$, 400 MHz): δ2.51-2.55 (m, 2H), 2.10-2.15 (m, 3H), 1.98-2.03 (m, 2H), 1.56-1.70 (m, 14H);
$^{13}$C NMR (CDCl$_3$, 100 MHz): δ159.8 (s), 134.1 (s), 124.4 (s), 118.3 (s), 108.1 (s), 34.2 (t), 31.1 (t), 30.8 (t), 29.4 (t), 27.9 (t), 27.5 (t), 26.0 (t), 22.9 (t), 22.7 (t), 20.4 (q).

Preparation of Mixture of 2-cycloheptylidene-2-(2-methylcyclohex-1-en-1-yl) acetonitrile and 2-cycloheptylidene-2-(6-methylcyclohex-1-en-1-yl)acetonitrile (92:8)

To a solution of nitrite compound obtained in step a) 1.50 g, 11.1 mmol, 1 equiv.) and cycloheptanone (6.28 g, 55.5 mmol, 5 equiv.) in NMP (33 mL) was added KOH (879 mg, 13.3 mmol, 1.2 equiv.) and the reaction was stirred at 80° C. for 29 h before being poured onto cracked ice. The reaction was quenched with a 10% aqueous solution of HCl and extracted three times with diethyl ether. The combined organic extracts were washed sequentially with water, a saturated solution of sodium bicarbonate, water and brine, dried over sodium sulfate and the solvent was evaporated. The residue was purified by flash column chromatography on silica gel (Heptane/AcOEt 99:1) and bulb-to-bulb distillation (0.048 mbar, 110-130° C.) to afford a mixture of regioisomers containing 2-cycloheptylidene-2-(2-methylcyclohex-1-en-yl)acetonitrile and 2-cycloheptylidene-2-(6-methylcyclohex-1-en-1-yl) acetonitrile (426 mg, 15% yield) as a colorless oil and in a 92:8 molar ratio.
Major isomer:
$^1$H NMR (CDCl$_3$, 400 MHz): δ2.63-2.65 (m, 2H), 2.24-2.29 (m, 2H), 1.98-2.02 (m, 2H), 1.47-1.72 (m, 17H);
$^{13}$C NMR (CDCl$_3$, 100 MHz): δ162.6 (s), 133.9 (s), 124.9 (s), 118.5 (s), 110.9 (s), 35.0 (t), 32.2 (t), 31.1 (t), 30.0 (t), 29.0 (t), 29.0 (t), 27.7 (t), 26.3 (t), 22.9 (t), 22.7 (t), 20.4 (q).

d) Preparation of Mixture of 2-cyclooctylidene-2-(2-methylcyclohex-1-en-1-yl) acetonitrile and 2-cyclooctylidene-2-(6-methylcyclohex-1-en-1-yl)acetonitrile (97:3)

To a solution of nitrile compound obtained in step a) (11.2 g, 83 mmol, 1 equiv.) and cyclooctanone (53.6 g, 416 mmol, 5 equiv.) in DMA (247 mL) was added t-BuOK (11.2 g, 120 mmol, 1.2 equiv.) and the reaction was stirred at 80° C. for 3.5 h before being poured onto cracked ice. The reaction was quenched with a 10% aqueous solution of HCl and extracted three times with diethyl ether. The combined organic extracts were washed sequentially with water, a saturated solution of sodium bicarbonate, water and brine, dried over sodium sulfate and the solvent was evaporated. The residue was purified by bulb-to-bulb distillation (0.014 to 115-140° C.), flash column chromatography on silica gel (Heptane/ AcOEt 99:1) and bulb-to-bulb distillation (0.014 mbar, 100-125° C.) to afford a mixture of regioisomers containing 2-cyclooctylidene-2-(2-methylcyclohex-1-en-1-yl)acetonitrile and 2-cyclooctylidene-2-(6-methylcyclohex-1-en-1-yl) acetonitrile (5.57 g, 28% yield) as a colorless oil and in a 97:3 molar ratio.
Major isomer:
$^1$H NMR, (CDCl$_3$, 400 MHz): δ2.64 (br s, 1H), 2.45 (br s, 1H), 2.08-2.29 (m, 3H), 2.01 (br s, 2H), 1.43-1.95 (m, 18H);
$^{13}$C NMR (CDCl$_3$, 100 MHz): δ163.9 (s), 134.1 (s), 124.8 (s), 118.6 (s), 110.5 (s), 33.1 (t), 32.3 (t), 31.1 (t), 28.8 (t), 28.7 (t), 28.1 (t), 25.8 (t), 25.4 (t), 23.3 (t), 22.9 (t), 22.7 (t), 20.5 (q).

e) Preparation of Mixture of 2-(2-methylcyclohex-1-en-1-yl)-2-(4-methylcyclohexylidene)acetonitrile and 2-(6-methylcyclohex-1-en-1-yl)-2-(4-methylcyclohexylidene)acetonitrile To a solution of nitrile compound obtained in step a) (3.00 g, 22.2 mmol, 1 equiv.) and 4-methylcyclohexanone (13.6 mL, 111 mmol, 5 equiv.) in NMP (15 mL) was added KOH (1.76 g, 26.6 mmol 1.2 equiv.) and the reaction was stirred at 80'C for 5 h before being quenched with a 5% aqueous solution of HCl and extracted three times with diethyl ether. The combined organic extracts were washed with brine, dried over sodium sulfate and the solvent was evaporated. The residue was purified by flash column chromatography on silica gel (Heptane/AcOEt 9911) and bulb-to-bulb distillation (0.37-0.52 mbar, 135-140° C.) to afford a mixture of regioisomers containing 2-(2-methylcyclohex-1-en-1-yl)-2-(4-methylcyclohexylidene) acetonitrile and 2-(6-methylcyclohex-1-en-1-yl)-2-(4- methylcyclohexylidene)acetonitrile (3.60 g, 71% yield) as a colorless oil.
MS: m/z.(+) 229.

f) Preparation of a Mixture of 2-(2-methylcyclohex-1-en-1-yl)-2-(3-methylcyclohexylidene) acetonitrile and 2-(6-methylcyclohex-1-en-1-yl)-2-(3-methylcyclohexylidene)acetonitrile To a solution of nitrite compound obtained in step a) (1.50 g, 11.1 mmol, 1 equiv.) and 3-methylcyclohexanone (6.81 mL, 55.5 mmol, 5 equiv.) in NMP (7.4 mL) was added KOH (879 mg, 13.3 mmol, 1.2 equiv.) and the reaction was stirred at 80° C. for 17 h before being quenched with a 5% aqueous solution of HCl and extracted three times with diethyl ether. The combined organic extracts were washed with brine, dried over sodium sulfate and the solvent was evaporated.

The residue was purified by flash column chromatography on silica gel (Heptane/AcOEt 99:1) and bulb-to-bulb distillation (0.17-0.21 mbar, 135-140° C.) to afford mixture of regioisomers containing 2-(2-methylcyclohex-1-en-1-yl)-2-(3-methylcyclohexylidene) acetonitrile and 2-(2-methylcyclohex-1-en-1-yl)-2-(3-methylcyclohexylidene) acetonitrile (1.16 g, 46% yield) as a colorless oil.

MS: m/z(+) 229.

g) Preparation of a Mixture of 2-(2-methylcyclohex-1-en-1-yl)-2-(2-methylcyclohexylidene) acetonitrile and 2-(6-methylcyclohex-1-en-1-yl)-2-(2-methylcyclohexylidene)acetonitrile To a solution of nitrile compound obtained in step a) (1.50 g, 11.1 mmol, 1 equiv.) and 2-methylcyclohexanone (6.80 mL 55.5 mmol, 5 equiv.) in NMP (33 mL) was added KOH (879 mg, 13.3 mmol, 1.2 equiv.) and the reaction was stirred at 80° C. for 3 days before being poured onto cracked ice. The reaction was quenched with a 10% aqueous solution of HCl and extracted three times with diethyl ether. The combined organic extracts were washed sequentially with water, a saturated solution of sodium bicarbonate, water and brine, dried over sodium sulfate and the solvent was evaporated. The residue was purified by flash column chromatography on silica gel (Heptane/AcOEt 99:1) and bulb-to-bulb distillation (0.08 mbar, 115-130° C.) to afford a mixture of regioisomers containing 2-(2-methylcyclohex-1-en-1-yl)-2-(2-methylcyclohexylidene)acetonitrile and 2-(6-methylcyclohex-1-en-1-yl)-2-(2-methylcyclohexylidene)acetonitrile (670 mg, 24% yield) as a colorless oil.

MS: m/z(+) 229.

Example 2

Preparation of a Perfuming Compound

A perfuming composition for softener, of the floral type, was prepared by admixing the following ingredients:

| Parts by weight | Ingredient |
| --- | --- |
| 100 | Hexyl Acetate |
| 300 | Benzyl Acetate |
| 150 | Carbinol Acetate |
| 30 | Cinnamic Alcohol |
| 300 | Anisic Aldehyde |
| 50 | C12 Aldehyde |
| 500 | Hexyl cinnamic Aldehyde |
| 40 | 2-methylundecanal |
| 30 | Aldehyde Supra |
| 20 | Calone ®[1] |
| 50 | Cetalox ®[2] |
| 200 | Citronellol |
| 300 | Clearwood ™[3] |
| 300 | Coranol[4] |
| 20 | γ-n-Decalactone |
| 100 | Delta Damascone |
| 200 | (1-ethoxyethoxy)cyclododecane |
| 200 | Geraniol |
| 230 | Habanolide ®[5] |
| 300 | Hedione [6] |
| 100 | Helvetolide ®[7] |
| 40 | Hivernal ®[8] |
| 10 | 10%* 1-Phenylvinyl acetate |
| 250 | Ionone Beta |
| 100 | Iralia ® Total[9] |
| 2000 | Iso E Super[10] |
| 20 | Isoeugenol Extra |
| 500 | Lilial[11] |
| 300 | Linalol |
| 200 | Lorysia ®[12] |
| 70 | Nirvanol ®[13] |
| 50 | Norlimbanol ®[14] |
| 20 | Rose oxid |
| 400 | Phenethylol |
| 40 | Phenoxyacetate Allyle |
| 100 | Phenylhexanol |
| 30 | Cis-3-Hexenol |
| 750 | Romandolide ®[15] |
| 10 | Ethyl Safrascenate |
| 450 | Amyle Salicylate |
| 150 | Terpineol |
| 50 | 10%* 2-ethyl-4,4-dimethyl-1-cyclohexanone |
| 40 | Triplal ®[16] |
| 100 | Undecavertol[17] |
| 80 | Vanilline Perf |
| 100 | Verdox ™[18] |
| 60 | 10%** Violettyne |
| 60 | 2-methoxynaphthalene |
| 100 | Ylang - 184110 D[19] |
| 9600 | |

*in dipropyleneglycol
**in isopropyle myristate
[1] 7-methyl-2H,4H-1,5-benzodioxepin-3-one; origin: Firmenich SA, Geneva, Switzerland
[2] dodecahydro-3a,6,6,9a-tetramethyl-naphtho[2,1-b]furan; origin: Firmenich SA, Geneva, Switzerland
[3] mixture of sesquiterpenes and alcohols present in patchouli oil; origin: Firmenich SA, Geneva, Switzerland
[4] 4-cyclohexyl-2-methyl-2-butanol; origin: Firmenich SA, Geneva, Switzerland
[5] pentadecenolide; origin: Firmenich SA, Geneva, Switzerland
[6] methyl dihydrojasmonate; origin: Firmenich SA, Geneva, Switzerland
[7] (1S,1'R)-2-[1-(3',3'-dimethyl-1'-cyclohexyl)ethoxy]-2-methylpropyl propanoate; origin: Firmenich SA, Geneva, Switzerland
[8] 3-(3,3/1,1-dimethyl-5-indanyl)propanal; origin: Firmenich SA, Geneva, Switzerland
[9] mixture of methylionones isomers; origin: Firmenich SA, Geneva, Switzerland
[10] 1-(octahydro-2,3,8,8-tetramethyl-2-naphthalenyl)-1-ethanone; origin: International Flavors & Fragrances, USA
[11] 3-(4-tert-butylphenyl)-2-methylpropanal; origin: Givaudan SA, Vernier, Switzerland
[12] 4-(1,1-dimethylethyl)-1-cyclohexyl acetate; origin: Firmenich SA, Geneva, Switzerland
[13] 3,3-dimethyl-5-(2,2,3-trimethyl-3-cyclopenten-1-yl)-4-penten-2-ol; origin: Firmenich SA, Geneva, Switzerland
[14] trans-1-(2,2,6-trimethyl-1-cyclohexyl)-3-hexanol; origin: Firmenich SA, Geneva, Switzerland
[15] (1S,1'R)-[1-(3',3'-dimethyl-1'-cyclohexyl)ethoxycarbonyl]methyl propanoate; origin: Firmenich SA, Geneva, Switzerland
[16] 2,4-dimethyl-3-cyclohexen-1-carboxaldehyde; origin: International Flavors & Fragrances, USA
[17] 4-methyl-3-decen-5-ol; origin: Givaudan SA, Vernier, Switzerland
[18] 2-tert-butyl-1-cyclohexyl acetate; origin: International Flavors & Fragrances, USA
[19] compounded perfumery base; origin: Firmenich SA, Geneva, Switzerland The addition of 400 parts by weight of mixture of regioisomer as described in. Example 1 to the above-described composition imparted to the latter a nice rosy and floral note with a slight orange blossom connotation. The mixture of regioisomer as described in Example 1 is a smart substituent to 2,2,2-trichloro-1-phenylethyl acetate which is a halide derivative.

Example 3

Preparation of a Perfuming Composition

A perfuming composition for detergent, of floral-rosy type, was prepared by admixing the following ingredients:

| Parts by weight | Ingredient |
| --- | --- |
| 160 | Hexyl Acetate |
| 400 | Phenylethyl Acetate |
| 80 | Styrallyl Acetate |
| 200 | Verdyl Acetate |
| 40 | Empetal[1] |
| 40 | Anisic Aldehyde |
| 80 | 2-methylundecanal |
| 200 | Benzylacetone |

| Parts by weight | Ingredient |
|---|---|
| 80 | Cetalox ®[2] |
| 300 | Citronellol |
| 500 | Coranol[3] |
| 50 | Coumarine |
| 40 | Damascenone |
| 80 | Dihydro Eugenol |
| 1200 | Dihydromyrcenol |
| 100 | Doremox ®[4] |
| 400 | Geraniol |
| 1000 | Hedione ®[5] |
| 90 | Hivernal ® Neo[6] |
| 100 | Isoeugenol Extra |
| 200 | Lavandin Grosso |
| 40 | Lemonile ®[7] |
| 800 | Linalol |
| 40 | Methyl Phenylethyl Ether |
| 40 | Methylparacresol |
| 200 | Phenethylol |
| 100 | Polywood ®[8] |
| 1200 | Hexyl Salicylate |
| 500 | Salicyline |
| 40 | Triplal ®[9] |
| 200 | Undecavertol[10] |
| 1000 | Vertofix ® Coeur[11] |
| 9500 | |

[1] 4(3)-(4-methyl-3-pentenyl)-3-cyclohexen-carbaldehyde; origin: Givaudan SA, Vernier, Switzerland
[2] dodecahydro-3a,6,6,9a-tetramethyl-naphtho[2,1-b]furan; origin: Firmenich SA, Geneva, Switzerland
[3] 4-cyclohexyl-2-methyl-2-butanol; origin: Firmenich SA, Geneva, Switzerland
[4] tetrahydro-4-methyl-2-phenyl-2H-pyran; origin: Firmenich SA, Geneva, Switzerland
[5] methyl dihydrojasmonate; origin: Firmenich SA, Geneva, Switzerland
[6] 3-(3,3/1,1-dimethyl-5-indanyl)propanal; origin: Firmenich SA, Geneva, Switzerland
[7] 3,7-dimethyl-2/3,6-nonadienenitrile; origin: Givaudan SA, Vernier, Switzerland
[8] 5,5,8a-trimethyldecahydronaphthalen-2-yl acetate; origin: Firmenich SA, Geneva, Switzerland
[9] 2,4-dimethyl-3-cyclohexen-l-carboxaldehyde; origin: International Flavors & Fragrances, USA
[10] 4-methyl-3-decen-5-ol; origin: Givaudan SA, Vernier, Switzerland
[11] methyl cedryl ketone; origin: International Flavors & Fragrances, USA The addition of 500 pans by weight of of mixture of regioisomer as described in Example 1 tote above-described composition improved perfume substantivity on dry laundry up to 3 days and imparted to the latter a nice floral and rosy note having an outstanding tenacity.

What is claimed is:

1. A compound of formula

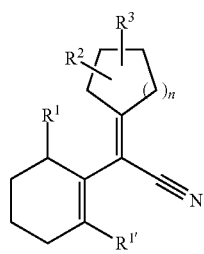

(I)

in the form of any one of its stereoisomers or a mixture thereof, and wherein $R^1$ and $R^{1'}$, independently from each other, represent a hydrogen atom or a methyl group provided that one of said groups represent a hydrogen atom and the other a methyl group; $R^2$ and $R^3$, independently from each other, represent substituents of the saturated ring and are a hydrogen atom or a $C_{1-3}$ alkyl group; and n is an integer varying between 1 and 4.

2. The compound according to claim 1, wherein said n is an integer varying between 1 and 2.

3. The compound according to claim 1, wherein $R^1$ represents a hydrogen atom and $R^{1'}$ represents a methyl group.

4. The compound according to claim 1, wherein $R^2$ represents a hydrogen atom or a methyl group and $R^3$ represents a hydrogen atom.

5. The compound according to claim 1, wherein the compound is in the form of a mixture of regioisomer containing 2-cyclohexylidene-2-(2-methylcyclohex-1-en-1-yl)acetonitrile and 2-cyclohexylidene-2-(6-methylcyclohex-1-en-1-yl)acetonitrile in a respective molar ratio of 94:6.

6. A perfuming composition comprising
   i) at least one compound of formula (I) of claim 1;
   ii) at least one ingredient comprising a perfumery carrier or a perfumery base; and
   iii) optionally at least one perfumery adjuvant.

7. A perfuming consumer product comprising at least one compound of formula (I) of claim 1.

8. The perfuming consumer product according to claim 7, wherein the perfumery consumer product is a perfume, a fabric care product, a body-care product, an air care product or a home care product.

9. The perfuming consumer product according to claim 7, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

10. A method to confer, enhance, improve or modify the odor properties of a perfuming composition or of a perfumed article, which method comprises adding to said composition or article an effective amount of at least one compound of claim 1.

* * * * *